United States Patent [19]
Wei et al.

[11] Patent Number: 5,765,577
[45] Date of Patent: *Jun. 16, 1998

[54] DENTAL FLOSS HOLDER

[76] Inventors: Kuang-Hsing Wei; Kuang-Hung Wei, both of 18500 Bay Leaf Way, Germantown, Md. 20874

[*] Notice: The term of this patent shall not extend beyond the expiration date of Pat. No. 5,570,710.

[21] Appl. No.: 698,734

[22] Filed: Aug. 16, 1996

Related U.S. Application Data

[63] Continuation-in-part of Ser. No. 528,889, Sep. 15, 1995, Pat. No. 5,570,710, and Ser. No. 581,372, Dec. 29, 1995, Pat. No. 5,653,246.

[51] Int. Cl.⁶ .................................................. A61C 15/00
[52] U.S. Cl. ................................................. 132/323; 132/321
[58] Field of Search ........................................ 132/321, 323, 132/324, 326, 327, 328, 329

[56] References Cited

U.S. PATENT DOCUMENTS

| | | | |
|---|---|---|---|
| 2,644,469 | 7/1953 | Cohen | 132/324 |
| 4,050,470 | 9/1977 | Miller | 132/323 |
| 4,403,625 | 9/1983 | Sanders et al. | 132/323 |
| 4,638,824 | 1/1987 | De La Hoz | 132/323 |
| 5,503,168 | 4/1996 | Wang | 132/323 |

*Primary Examiner*—Gene Mancene
*Assistant Examiner*—Pedro Philogene

[57] ABSTRACT

A dental floss holder for securely fastening one end of a dental floss instead of winding it around a finger includes a first member, at least one pair of matching surfaces, a second member, and thread segments for locking the first and second members together. One of the matching surfaces is formed on the first member and the other on the second member. When the first and second members lock together, the dental floss is securely fastened between at least one pair of the matching surfaces. Also, a slot is provided for facilitating the retention of the floss.

19 Claims, 2 Drawing Sheets

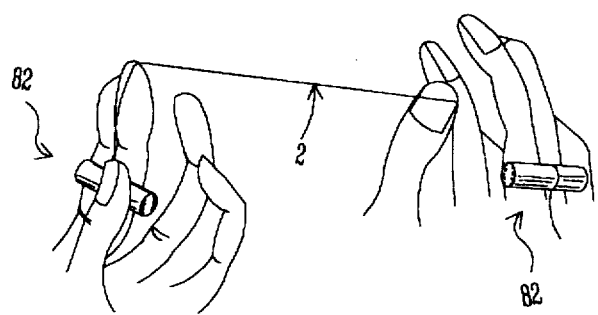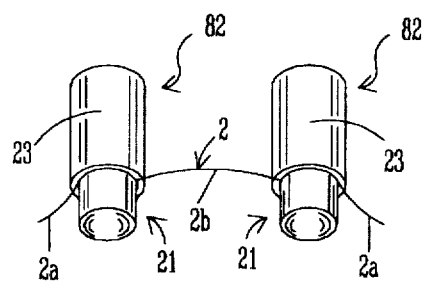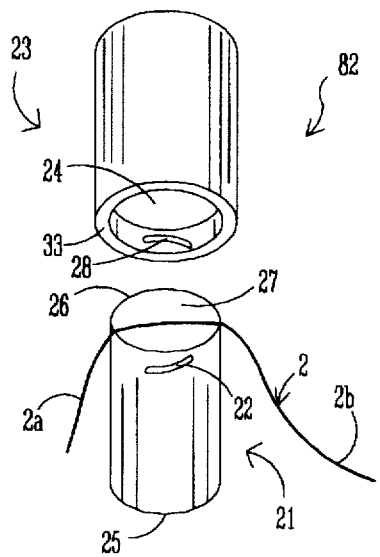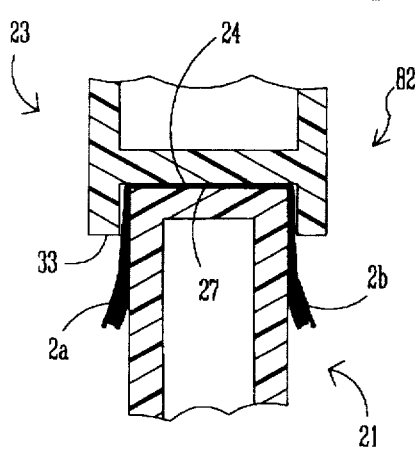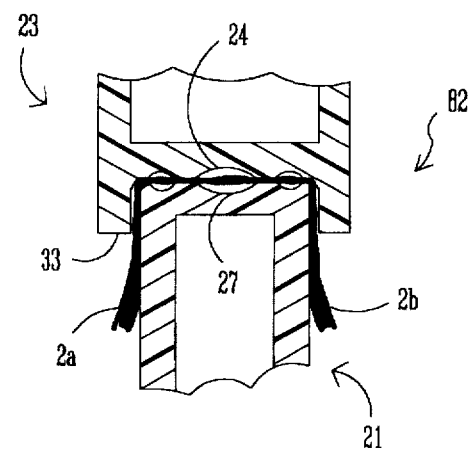
FIG. 1. (left) (right)  FIG. 2.
FIG. 3.
FIG. 4.  FIG. 5.

DENTAL FLOSS HOLDER

CROSS REFERENCE TO RELATED APPLICATIONS

This Application is a continuation-in-part of U.S. applications Ser. No. 08/528,889 filed Sep. 15, 1995, U.S. Pat. No. 5,570,710 and Ser. No. 08/581,372 filed Dec. 29, 1995 U.S. Pat. No. 5,653,246.

BACKGROUND OF THE INVENTION

1. The Field of the Invention

This invention relates to the teeth cleaning with a length of dental floss and provides as its general object an improved device which is used to securely fasten dental floss and to render teeth-cleaning more effectively.

2. Description of the Prior Art

There are many devices attempting to render flossing less tedious and make it more effective and convenient. Moreover, a growing number of dentists and orthodontists recommend highly for cleaning teeth daily by using dental floss to remove food particles between teeth. However, most people still don't floss daily, even those who take teeth-cleaning and dental care seriously. The inconvenience and discomfort for maneuvering the dental floss by winding ends of a length of dental floss around two fingers is the main reason. The winding ends of a length of dental floss around two fingers will not only cause discomfort on fingers but also render difficulties in manipulating in mouth. Although there are numerous devices with a predetermined length of floss fixed in a two-pronged dental device, maneuvering with two fingers winding a length of dental floss is still the most effective way of daily dental floss cleaning, especially for reaching and positioning between the rear most teeth, and is highly recommended by the dental profession. U.S. Pat. No. 4,050,470 to Miller (1977) provides a dental floss holder with an inwardly tapered slot extending along one elongate edge which does not fasten the dental floss securely in place to facilitate the manipulating of the floss in mouth. U.S. Pat. No. 4,638,824 to De La Hoz (1987) provides a pair of dental floss finger rings having three cut out prongs for retaining a length of dental floss. The retaining prongs are prone to cut the floss at the retaining point as a result of strong force applied during flossing. Also, the floss tends to be pull out of the prongs during flossing operation which requires different angles for inserting floss in between teeth at different positions.

SUMMARY OF THE INVENTION

It is a general object of the invention to provide a dental floss holder and a method for fastening one end of a dental floss. A dental floss holder for securely fastening one end of a dental floss instead of winding it around a finger includes a first member, at least one pair of matching or corresponding surfaces, a second member, and locking means. One of the matching surfaces is formed on the first member and the other matching surface on the second member. When the first and second members lock together, the dental floss is securely fastened therebetween.

The method of the invention includes first retaining the dental floss on the first member. It then follows with locking the second member with the first member so as to lock at least one pair of matching surfaces together to securely fasten the dental floss therebetween.

Accordingly, several objects and advantages of the present invention are:

(a) to provide an improved dental floss holder which is used to eliminate the discomfort caused by winding a length of dental floss around fingers;

(b) to provide an improved dental floss holder which is designed to save the wasteful of floss for winding an extra length of dental floss around fingers;

(c) to provide an improved dental floss holder for securely fastening dental floss ends than winding around fingers, which is needed to be rewound several times during the course of teeth-cleaning; and (d) to provide an improved dental floss holder to better control of a strained floss and perform a more effective teeth-cleaning.

Further objects and advantages of the invention will become apparent from the appended drawings and the ensuing specifications.

DRAWING FIGURES

FIG. 1 is a perspective view showning the use of the dental floss holders with a dental floss fastened in each holder;

FIG. 2 is a perspective view of the dental floss holders, shown in FIG. 1, connecting in a pair with a dental floss;

FIG. 3 is a perspective view of the dental floss holder, with the first member being separated from the second member;

FIG. 4 is a fragmentary sectional view showing details of a portion of the dental floss fastened in the dental floss holder of FIG. 3 in a locked position, taken on an enlarged scale for clarity.

FIG. 5 is a view similar to FIG. 4, except that the forms of the matching surfaces are different.

DETAILED DESCRIPTION OF THE PREFERRED EMBODIMENT

Figure 6:
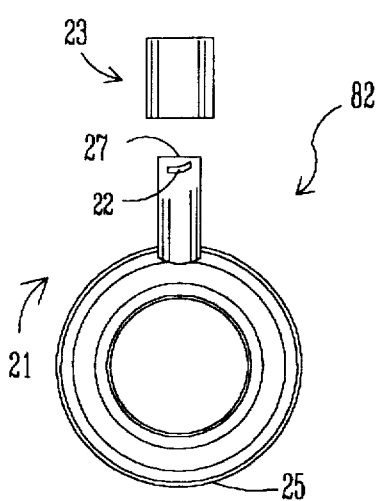
FIG. 6 is a front view of an embodiment similar to that of FIG. 3, except with a ring shape on the first member.

Referring to FIGS. 1 and 2, it illustrates that a length of conventional dental floss 2 connects two identical dental floss holders 82. Dental floss 2 includes a middle section 2b and two end sections 2a. Each end section 2a defines each end portion of dental floss 2 extending out from dental floss holder 82. Middle section 2b defines the portion of dental floss 2 between dental floss holders 82 and connects both holders 82. Each dental floss holder 82 is easily manipulated by each hand so that dental floss 2 is ready to be used inside mouth to clean teeth (not shown) as one usually does with both ends of a dental floss winding around fingers. One of dental floss holders 82 may be held inside one hand (left of FIG. 1), and the other holder may be supported by the back of the other hand (right of FIG. 1) to clean teeth. Dental floss holders 82 provide much better control of dental floss 2 and eliminate the discomfort by winding ends of a dental floss around fingers. A single holder may be used on one hand with the opposite end of the dental floss fastened by some other means or by fingers; however, it is expected that two holders will be used. Dental floss holder 82 is suitable for use with the conventional thread or cord type of dental floss or with ribbon or band type of floss. It should be understood that the term "dental floss" is used generically to indicate any type of floss. Referring to FIGS. 3 and 4, each dental floss holder 82 comprises a first member 21 which preferably comprises a generally elongated cylindrical piece of material dimensioned to be easily handled by fingers for retaining dental floss 2 on first member 21. First member 21 has a first end 26 and a second end 25. First member 21 also has a plurality of spaced thread segments 22. Each thread segment 22 has the same pitch, starts at the same height, and ends at the same lower height on first member 21. In this example, it provides two equally spaced external thread segments 22, each extending about 75–90° on the outer circumference of first member 21. However, the number of thread segments can be selected as required and the angular extent can be obtained accordingly. First member 21 further comprises a first outer surface 27. First outer surface 27 is preferably integrally formed on first member 21 at first end 26.

Referring still to FIGS. 3 and 4, each dental floss holder 82 comprises a second member 23. Second member 23 comprises preferably a generally elongated cylindrical piece of material and is also dimensioned to be easily handled by fingers. Second member 23 comprises internal thread segments 28 that are dimensioned to mate with external thread segments 22. Second member 23 comprises a third outer surface 33. Second member 23 also comprises an inner surface 24 that is the matching surface of first outer surface 27 so that when inner and first outer surfaces 24 and 27 abut against each other, dental floss 2 is compressed tightly therebetween. As shown in FIG. 4, the cross-sectional dimension of dental floss 2 is compressed between surfaces 24 and 27 when first and second members 21 and 23 lock together. Therefore, the closely abutted surfaces 24 and 27 are to effectively fasten the compressed dental floss 2 therebetween.

Dental floss holder 82 of FIG. 5 is similar to that of FIG. 4, except that inner and first outer surfaces 24 and 27 are of the form of small ridges or corrugations. Otherwise, holder 82 in FIG. 5 is identical to that in FIG. 4 in operation, in resultant effects, and generally in structure. In FIGS. 4 and 5, it shows that the length of engagement between dental floss 2 and inner and first outer surfaces 24 and 27 can be of any length, as required by different forms of surfaces. Therefore, the length of engagement is dimensioned such that dental floss 2 is securely fastened therebetween.

Dental floss holder 82 of FIG. 6 is similar to that of FIG. 3, except that first member 21 comprises substantially the form of a ring which is adapted to fit a finger so that the ring may be inserted into a finger when cleaning teeth. Similarly, second member 23 may also comprise substantially the form of a ring as required. Otherwise, holder 82 in FIG. 6 is identical to that in FIG. 3 in operation, in resultant effects, and generally in structure.

Figure 7:
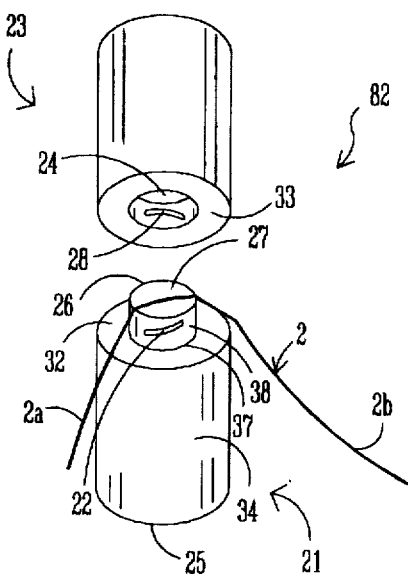
FIG. 7 is a perspective view of an embodiment similar to that of FIG. 3, except that the first and second members provide a second pair of matching surfaces.
Figure 8:
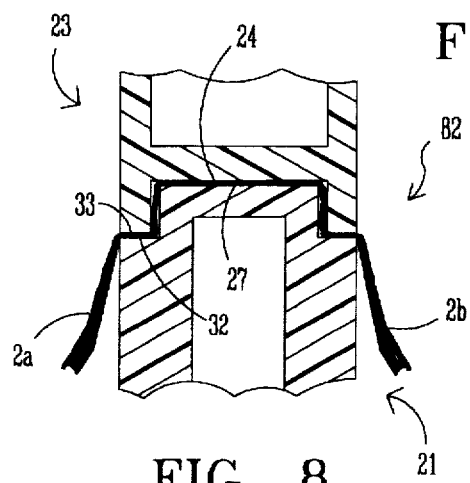
FIG. 8 is a fragmentary sectional view showing details of a portion of the dental floss fastened in the dental floss holder of FIG. 7 in a locked position, taken on an enlarged scale for clarity.

Dental floss holder 82 of FIGS. 7 and 8 are similar to that of FIGS. 3 and 4, except that third outer surface 33 has a bigger diameter, and first member 21 has a top 38 and a bigger diameter base 34. Top 38 connects to base 34 at a third end 37. Base 34 has a second outer surface 32 which is the matching surface of third outer surface 33. The matching surfaces 32 and 33 are dimensioned such that when first and second members 21 and 23 are locked together by locking means, dental floss 2 is securely fastened between not only surfaces 24 and 27 but also surfaces 32 and 33. In this example, the locking means is thread segments 22 and 28.

Figure 9:
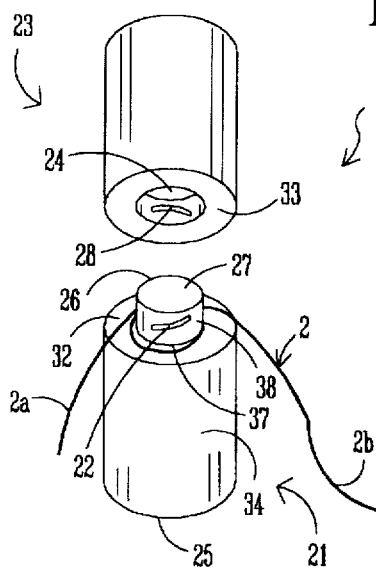
FIG. 9 is a view similar to FIG. 7, except that the dental floss circles or wraps around a top on the first member.

Dental floss holder 82 of FIG. 9 is identical to that of FIG. 7, except that dental floss 2 circles or wraps around top 38 substantially near third end 37. The wrapping around top 38 enhances the fastening of dental floss 2 between second and third outer surfaces 32 and 33. Although dental floss 2 is fastened between surfaces 32 and 33 only, wrapping dental floss 2 around top 38 and locking dental floss 2 between surfaces 32 and 33 produce the same fastening results as described in FIG. 7. However, without wrapping dental floss 2 around top 38 in this example is still workable.

Figure 10:
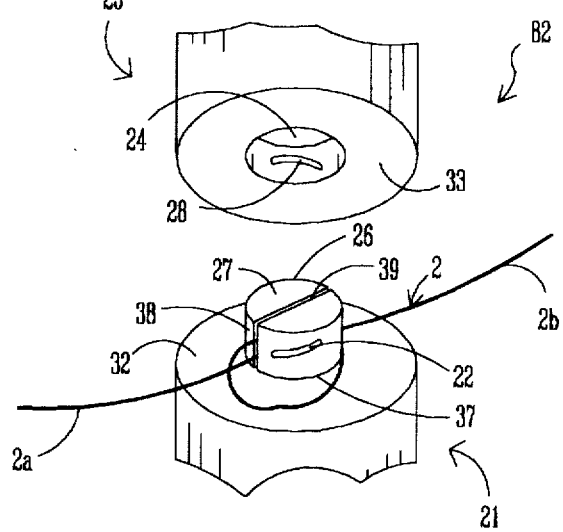
FIG. 10 is a fragmentary view of an embodiment similar to that-of FIG. 9, except that the top has a slot.

Dental floss holder 82 of FIG. 10 is similar to that of FIG. 9, except that top 38 has a slot 39. Slot 39 is a strip of a narrow cut toward substantially third end 37, creating generally two parallel lines adjacent to each other closely, and dividing top 38 into two substantially semi-circular configurations. The perpendicular distance between the two parallel lines may be slightly smaller than, equal to, or slightly larger than the cross-sectional dimension of dental floss 2. The preferable distance between the two parallel lines of slot 39 is dimensioned to be slightly smaller than the cross-sectional dimension of dental floss 2 so that it effectively receives dental floss 2. Dental floss 2 may insert into slot 39 and wrap around top 38 substantially near third end 37. This adds enhancement to fasten dental floss 2.

The method of fastening one end of dental floss 2 according to the invention may be best described with reference to FIGS. 3, 7, 9, and 10. The method includes first placing or retaining one end of dental floss 2 on first member 21 at first end 26 with end section 2a substantially near second end 25 along one side of first member 21 and middle section 2b along the other side of first member 21 so that dental floss 2 extends from end section 2a substantially near second end 25, reaches generally longitudinally to first end 26 along one side of first member 21, crosses generally transversely over first member 21 at first end 26, and then extends generally longitudinally toward second end 25 along the other side of first member 21 to middle section 2b. Dental floss 2 may be held by fingers against first member 21 on both sides to facilitate the fastening of dental floss 2. Alternatively, dental floss 2 may cross over only third end 37 without reaching first end 26 and may also wrap around top 38. Alternatively, dental floss 2 may insert into slot 39 and may wrap around top 38.

Having dental floss 2 retained on first member 21 with sections 2a and 2b on both sides of first member 21, the method continues with the step of engaging or locking second member 23 with first member 21 so as to lock inner and first outer surfaces 24 and 27, or second and third outer surfaces 32 and 33, or both inner and first outer surfaces 24 and 27 as well as second and third outer surfaces 32 and 33 tightly together so that dental floss 2 is securely fastened between at least one pair of the matching surfaces. In this example, the locking means is the mating thread segments 22 and 28. The locking means can be of any locking or clamping devices such that dental floss 2 is securely fastened between at least one pair of the matching surfaces.

Although the description above contains many specifications, these should not be construed as limiting the scope of the invention but as merely providing illustrations of some of the presently preferred embodiments of this invention. Thus the scope of the invention should be determined by the appended claims and their legal equivalents, rather than by the examples given.

We claim:

1. A dental floss holder for fastening a dental floss, said holder comprising:
   a first member;
   a second member;
   a pair of matching outer surfaces, said outer surfaces being engageable with each other to fasten the floss therebetween, one of said outer surfaces formed on said first member, the other of said outer surfaces formed on said second member; and
   locking means for locking said first and second members together so that the floss is fastened between said outer surfaces, whereby said holder having the floss fastened therein is manipulated by a hand in lieu of winding the floss around a finger for teeth cleaning.

2. The holder of claim 1, wherein said locking means comprises internal thread segments and external thread segments, said internal and external thread segments being threadably engageable with each other.

3. The holder of claim 1, wherein one of said first and second members comprises a slot defining an opening cut thereacross substantially at one end thereof.

4. The holder of claim 1, wherein one of said first and second members comprises a slot defining an opening cut thereacross substantially at one end thereof, said slot having a substantially perpendicular distance therebetween, said distance selected from a range between substantially equal to the cross section of the floss and substantially equal to zero.

5. The holder of claim 1, wherein at least one of said first and second members comprises a configuration adapted to be handled by fingers, whereby the floss may be held against both sides of said one of said first and second members to facilitate the retention of the floss, said configuration selected from the group consisting of:
   (a) a substantially ring-shaped configuration adapted to be fitted into a finger;
   (b) a substantially cylindrical configuration; and
   (c) a substantially elongated configuration.

6. The holder of claim 1 wherein said outer surface formed on said first member is a second outer surface and said matching outer surface formed on said second member is a third outer surface.

7. A dental floss device for fastening a length of dental floss, said device comprising:
   two separate dental floss holders for fastening the floss in a spaced apart relationship, at least one of said holders comprising:
      a first member;
      a second member;
      a pair of matching outer surfaces, said outer surfaces being engageable with each other to fasten the floss therebetween, one of said outer surfaces formed on said first member, the other of said outer surfaces formed on said second member; and
      locking means for locking said first and second members together so that the floss is fastened between said outer surfaces, whereby each of said holders having the floss fastened therein is manipulated by a hand in a spaced apart relationship for teeth cleaning.

8. The device of claim 7, wherein said locking means of said at least one of said holders comprises internal thread segments and external thread segments, said internal and external thread segments being threadably engageable with each other.

9. The device of claim 7, wherein one of said first and second members of said at least one of said holders comprises a slot defining an opening cut thereacross substantially at one end thereof.

10. The device of claim 7, wherein one of said first and second members of said at least one of said holders comprises a slot defining an opening cut thereacross substantially at one end thereof, said slot having a substantially perpendicular distance therebetween, said distance selected from a range between substantially equal to the cross section of the floss and substantially equal to zero.

11. The device of claim 7, wherein at least one of said first and second members of said at least one of said holders comprises a configuration adapted to be handled by fingers, whereby the floss may be held against both sides of said one of said first and second members to facilitate the retention of the floss, said configuration selected from the group consisting of:
   (a) a substantially ring-shaped configuration adapted to be fitted into a finger;
   (b) a substantially cylindrical configuration; and
   (c) a substantially elongated configuration.

12. The device of claim 7, wherein said outer surface formed on said first member is a second outer surface and said matching outer surface formed on said second member is a third outer surface.

13. A method of fastening a dental floss, comprising the steps of:
   placing the floss on one of a first member and a second member, said one member having an outer surface thereon, the other of said first member and said second member having a matching outer surface thereon, said matching surfaces being engageable with each other to fasten the floss therebetween; and
   locking said first and second members together so that the floss is fastened between said surfaces, whereby said first and second members having the floss fastened therein are manipulated by a hand in lieu of winding the floss around a finger for teeth cleaning.

14. The method of claim 13, wherein the placing step is performed by retaining the floss in a manner selected from the group consisting of:
   (a) extending from substantially one side of said one member over said outer surface to substantially the other side of said one member,
   (b) extending from substantially one side of said one member to said outer surface, wrapping around a top, and extending to substantially the other side of said one member,
   (c) extending from substantially one side of said one member over a first end of said top to substantially the other side of said one member,
   (d) extending from substantially one side of said one member to a slot and extending through said slot to substantially the other side of said one member, and
   (e) extending from substantially one side of said one member to said slot, extending through said slot, wrapping around said top at least once from side to side, and extending through said slot to either side of said one member,
   whereby the floss may be held against both sides of said one member to facilitate the retention of the floss on said one member.

15. The method of claim 13, wherein the locking step is performed by screwing together internal and external thread segments.

16. The method of claim 13, wherein said outer surface formed on said first member is a second outer surface and said matching outer surface formed on said second member is a third outer surface.

17. A method of fastening a dental floss, comprising the steps of:

retaining the floss on a second outer surface of a first member, whereby the floss may be held against said first member to facilitate the retention of the floss on said first member, a second member having a matching outer surface, said matching outer surfaces being engageable with each other to fasten the floss therebetween; and locking said first and second members together so that the floss is fastened between said outer surfaces, whereby said first and second members having the floss fastened therein are manipulated by a hand in lieu of winding the floss around a finger for teeth cleaning.

18. The method of claim 17, wherein the locking step is performed by screwing together internal and external thread segments.

19. The method of claim 17, wherein the retaining step is performed by retaining the floss in a manner selected from the group consisting of:

(a) extending from substantially one side of said first member over said outer surface to substantially the other side of said first member, (b) extending from substantially one side of said first member to said outer surface, wrapping around a top, and extending to substantially the other side of said first member, (c) extending from substantially one side of said first member over a first end of said top to substantially the other side of said first member, (d) extending from substantially one side of said first member to a slot and extending through said slot to substantially the other side of said first member, and (e) extending from substantially one side of said first member to said slot, extending through said slot, wrapping around said top at least once from side to side, and extending through said slot to either side of said first member.

* * * * *